United States Patent [19]
Holko

[11] Patent Number: 5,358,547
[45] Date of Patent: Oct. 25, 1994

[54] COBALT-PHOSPHOROUS-BASE WEAR RESISTANT COATING FOR METALLIC SURFACES

[76] Inventor: Kenneth H. Holko, 7384 Trade St., San Diego, Calif. 92121-2422

[21] Appl. No.: 19,256

[22] Filed: Feb. 18, 1993

[51] Int. Cl.$^5$ .................. C22C 19/07; B32B 15/00
[52] U.S. Cl. .................... 75/254; 75/255; 428/668; 428/679
[58] Field of Search .......... 75/255, 254; 428/668, 428/679; 420/435, 436, 440

[56] References Cited

U.S. PATENT DOCUMENTS

| | | | |
|---|---|---|---|
| 2,159,805 | 5/1939 | Lenz et al. | 420/435 |
| 2,200,743 | 5/1940 | Hardey | 420/435 |
| 2,643,221 | 6/1953 | Brenner et al. | 420/435 |
| 3,035,934 | 5/1962 | Cape | 420/436 |
| 3,047,382 | 7/1962 | Harpster | 420/436 |
| 3,155,491 | 11/1964 | Hoppin et al. | 75/255 |
| 3,313,633 | 4/1967 | Longo | 420/436 |
| 3,497,347 | 2/1970 | Dautzenberg et al. | 75/255 |
| 4,381,944 | 5/1983 | Smith et al. | 75/255 |
| 5,149,597 | 9/1992 | Holko | 428/679 |

FOREIGN PATENT DOCUMENTS

| | | | |
|---|---|---|---|
| 697416 | 11/1964 | Canada | 75/255 |
| 487263 | 6/1938 | United Kingdom | 420/435 |

*Primary Examiner*—John Zimmerman
*Attorney, Agent, or Firm*—H. Jay Spiegel

[57] ABSTRACT

A wear resistant coating includes a mixture or compound of Cobalt and Phosphorous either alone or mixed with one or more alloys to provide a coating for metallic surfaces rendering the metallic surfaces more resistant to wear. A preferred combination of Cobalt and Phosphorous utilized in the present invention consists of 89%, by weight, Cobalt and 11%, by weight, Phosphorous, which combination is at approximately the "eutectic" ratio, that is, that combination of Cobalt and Phosphorous exhibiting the lowest melting point. Preferred environments of application of the inventive coating include surgical blades, files and burrs, guide slots, drills and drill guides, surgical instruments and medical prostheses and for abrasive particles. The subject coatings have achieved a micro-hardness of 1500 DPH (Diamond Pyramid Hardness), approximately equal to the Rockwell C75 hardness.

9 Claims, 3 Drawing Sheets

COBALT-PHOSPHOROUS-BASE WEAR RESISTANT COATING FOR METALLIC SURFACES

BACKGROUND OF THE INVENTION

Firstly, Applicant wishes to incorporate by reference Applicant's prior U.S. Pat. No. 5,149,597 as well as U.S. Pat. No. 5,135,533 for which Applicant herein is a copatentee. U.S. Pat. No. 5,149,597 discloses a Nickel-based wear resistant coating for metallic surfaces. U.S. Pat. No. 5,135,533 discloses improvements in surgical saw blades as well as use of the same Nickel-based coating to coat such saw blades to render them more wear resistant.

The wear resistant coatings disclosed in U.S. Pat. Nos. 5,135,533 and 5,149,597 have been successfully utilized in coating surgical saw blades. However, a portion of the population can have an allergic reaction to Nickel and Nickel-containing materials. While no such allergic reactions have yet occurred through use of the coatings disclosed in U.S. Pat. Nos. 5,135,533 and 5,149,597, the perception that such allergic reactions could occur has created a need to develop a wear resistant coating at least as effective as that which is disclosed in U.S. Pat. Nos. 5,135,533 and 5,149,597 but wherein the predominant materials do not include or at least minimize Nickel. It is with this goal in mind that the present invention was developed.

SUMMARY OF THE INVENTION

The present invention relates to a Cobalt-Phosphorous-base wear resistant coating for metallic surfaces. The said wear resistant coating is disclosed in numerous embodiments hereinafter. A summary of these embodiments is as follows:

(A) In a first aspect, Applicant has developed a coating alloy consisting of 89%, by weight, Cobalt and 11%, by weight, Phosphorous. This combination, by weight, is at approximately the "eutectic" composition of these elements. At the "eutectic" composition, the combination of elements exhibits the lowest possible melting point. Applicant has chosen this ratio because the lower the melting point of the alloy, the lesser the chance that the coated substrate will be damaged during the coating process. Hereinafter, this alloy is termed "CoP".

(B) In a further aspect, the "CoP" alloy may be combined with up to 25%, by weight, of any one of various Nickel-based alloys as will be described in greater detail hereinafter. The coating alloys so formed include only a small percentage of Nickel and, as such, are unlikely to promote allergic reactions.

(C) In a further aspect, Applicant has developed coating alloys including a mixture of "CoP" and 15–50%, by weight, Cobalt powder, a mixture of "CoP" and 50%, by weight, Titanium Carbide applied and then overcoated with "CoP", a mixture of "CoP" and 50%, by weight, Tungsten Carbide/Cobalt binder applied and then overcoated with "CoP", a mixture of "CoP" and 50%, by weight, T-400 powder applied and then overcoated with "CoP", a mixture of "CoP" and 50%, by weight, Palladium powder, a mixture of "CoP" and 50%, by weight, Platinum powder, a mixture of "CoP" and 25–50%, by weight, of an alloy comprising 73%, by weight, Titanium and 27%, by weight, Cobalt, and a mixture of "CoP" and 20–40%, by volume, hydroxylapatite powder. Other mixtures which form a part of the present invention as described hereinafter have been found to be effective as coating compositions.

(D) Applicant has also employed the intermetallic compound "$Co_2P$" as a coating composition. Additionally, Applicant has found that a mixture of "$Co_2P$" and 25–50%, by weight, Amdry 400 alloy create an effective coating.

As such, it is a first object of the present invention to provide a Cobalt-Phosphorous-base wear resistant coating for metallic surfaces.

It is a further object of the present invention to provide such a coating in various embodiments including embodiments employing "CoP" and embodiments employing "$Co_2P$".

It is a still further object of the present invention to provide such a coating useful in coating surgical saw blades, files and burrs.

It is a still further object of the present invention to provide such a coating useful in other applications including surgical instruments and prostheses, bearing surfaces, oil well drilling and pumping equipment.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
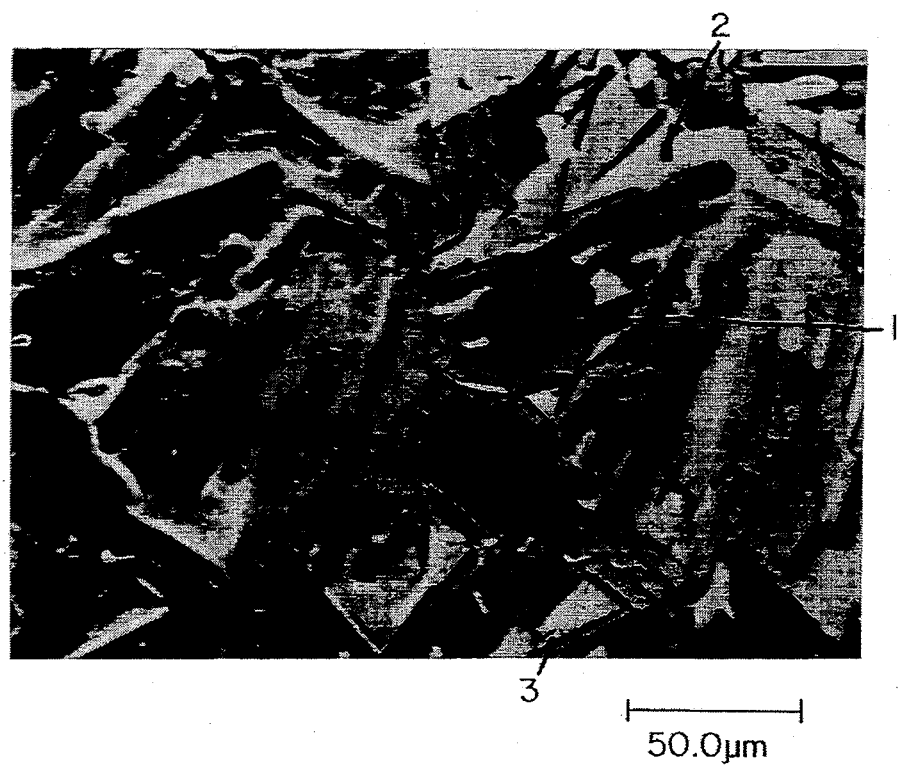
FIG. 1 shows a photomicrograph of a surgical saw blade substrate coated with a mixture of "CoP" and 25%, by weight, Nicrobraz 50.

In this section, numerous known alloys will be discussed in terms of their respective associations with certain aspects and embodiments of the present invention. In Table A, below, these alloys are listed along with the percents, by weight, of their respective ingredients. Table A is as follows:

TABLE A

| Tradename | Manufacturer | Ni | Co | Cr | P | Si | B | Fe | C | Mo | W |
|---|---|---|---|---|---|---|---|---|---|---|---|
| Nicrobraz 50 | Wall Colmonoy | Bal | 0 | 14 | 10 | 0 | 0 | 0 | 0 | 0 | 0 |
| Nicrobraz 125 | Wall Colmonoy | Bal | 0 | 14 | 0 | 4.5 | 3 | 4.5 | .7 | 0 | 0 |
| Nicrobraz 135 | Wall Colmonoy | Bal | 0 | 0 | 0 | 3.5 | 1.9 | 0 | .06 | 0 | 0 |
| Nicrobraz 51 | Wall Colmonoy | Bal | 0 | 25 | 10 | 0 | 0 | 0 | 0 | 0 | 0 |
| Amdry 100 | Sulzer Plasma | Bal | 0 | 19 | 0 | 10 | 0 | 0 | 0 | 0 | 0 |
| Amdry 915 | Sulzer Plasma | Bal | 0 | 13 | 0 | 4 | 2.8 | 4 | 0 | 0 | 0 |

TABLE A-continued

| Tradename | Manufacturer | Constituent Ingredients, % by weight | | | | | | | | | |
|---|---|---|---|---|---|---|---|---|---|---|---|
| | | Ni | Co | Cr | P | Si | B | Fe | C | Mo | W |
| Amdry 400 | Sulzer Plasma | 17 | Bal | 19 | 0 | 8 | 0 | 0 | .4 | 0 | 4 |
| Tribaloy-400 | Deloro Stellite | 0 | Bal | 8 | 0 | 2.5 | 0 | 0 | .04 | 28 | 0 |

In a first aspect of the present invention, a near "eutectic" composition of Cobalt and Phosphorous has been developed for coating applications. This composition comprises 89%, by weight, Cobalt and 11%, by weight, Phosphorous. As explained above, the "eutectic" composition is that combination of Cobalt and Phosphorous which exhibits the lowest melting point of any combination of these elements. The "eutectic" composition is preferably employed because the lower the melting point of the composition, the less likely that damage will result in the substrate during the coating process.

A first method of making the "CoP" composition consists of an atomization process. In this process, an electrode of 89%, by weight, Cobalt and 11%, by weight, Phosphorous is created by melting this composition in a refractory crucible and allowing solidification to occur. The end of the solid electrode is then arc melted while the electrode is spinning at high speed. Small spheroidal particles are expelled from the end of the electrode with each such particle having the composition of 89%, by weight, Cobalt and 11%, by weight, Phosphorous. The particles are then solidified utilizing either inert gas or water. The process is preferably undertaken in an inert atmosphere with the particles being collected and graded according to size. These particles may then be employed in the coating process as disclosed herein.

Alternatively, the powder particles may also be produced by crushing a melt that is cast and solidified in a crucible. The melt is made by mixing starting stock in the proportions of 89%, by weight, Cobalt and 11%, by weight, Phosphorous. Melting may be accomplished in a variety of ways including through induction heating, arc melting, radiant heating from resistance heaters and the use of an electron beam. Preferably, melting is carried out in an inert gas atmosphere or within a flux blanket to protect the melt from oxidation.

If desired, the "CoP" composition and other lower percent, by weight, Phosphorous compositions may also be produced as a plating on the surface of the parts to be coated or joined. Electroless or electrolytic deposition may be carried out from a chemical bath formulated to produce "CoP".

In a further aspect of the present invention, it is possible to utilize the compound "Co$_2$P" by reacting Cobalt and Phosphorous powders that have been premixed. The premixed powders are heated in an inert atmosphere until the reaction temperature is achieved. The reaction is exothermic and self-sustaining. Any unreacted powder may easily be separated from the "Co$_2$P" which is formed. In accordance with the teachings of the present invention, numerous coating compositions have been developed. Table B lists all of the coating compositions which are contemplated in accordance with the teachings of the present invention. The identifying number for each composition will be used in the description hereinafter.

TABLE B

| Alloy Number | Ingredients, % by weight | | Notes |
|---|---|---|---|
| 1 | 89% Co | 11% P | Termed CoP herein |
| 2 | 79.19% Co | 20.81% P | The Compound Co$_2$P |
| 3 | 97% Co | 3% P | |
| 4 | 75–90% CoP | 10–25% Nicrobraz 50 | |
| 5 | 75% CoP | 25% Nicrobraz 125 | |
| 6 | 75% CoP | 15% Nicrobraz 50 and 10% Nicrobraz 125 | |
| 7 | 75% CoP | 25% Nicrobraz 135 | |
| 8 | 75% CoP | 25% Nicrobraz 51 | |
| 9 | 75% CoP | 25% Amdry 100 | |
| 10 | 75% CoP | 25% Amdry 915 | |
| 11 | 50–75% Co$_2$P | 25–50% Amdry 400 | |
| 12 | 50–85% CoP | 15–50% Co Powder | |
| 13 | 50% CoP | 50% Titanium Carbide | Applied, then overcoated with CoP |
| 14 | 50% CoP | 50% Tungsten Carbide/Cobalt binder | Applied, then overcoated with CoP |
| 15 | 50% CoP | 50% T-400 Powder | Applied, then overcoated with CoP |
| 16 | 50% CoP | 50% Pd Powder | |
| 17 | 50% CoP | 50% Pt Powder | |
| 18 | 50–75% CoP | 25–50% Ti—Co Powder Crystalline and amorphous forms | 73% Ti, 27% Co |
| 19 | 60–80% (% by volume) CoP | 20–40% (% by volume) hydroxylapatite powder Crystalline and amorphous forms | |

Alloys 1 and 3–19 comprise coating alloys while "alloy" 2 comprises the compound "Co$_2$P". These alloys may be employed for coating and/or joining of metallic and ceramic materials and may be applied in the form of powder, foil, wire, and/or electroplated or electroless deposited form. The various alloys and the compound "Co$_2$P" have incipient melting or solidus temperatures of 1610° F. to 1900° F. and brazing temperatures of from 1900° F. to 2075° F. During heating and melting of these substances, environments such as vacuum or inert gas atmospheres are employed to protect them and the coated substrate from oxidation or other contamination.

The alloys set forth in Table B utilize the addition of Phosphorous as a melting point depressant either singly or in combination with other melting point depressants. As should be understood from Table B, the base alloy "CoP" or intermetallic compound "Co$_2$P" may be used either singly or in combination with the other commercially available alloys as set forth in Table B, to produce a variety of aesthetic appearances and properties.

Advantages of the alloys described in Table B over previously known Cobalt base alloys include lower application temperatures, formation of metal phosphides which are hard and lubricious, as well as minimization of inclusion of elements which may be undesirable in some applications. For example, as described above, some people exhibit allergic reactions to exposure to Nickel. As such, even in those alloys described in Table B which include Nickel-based alloys, the percent of Nickel in the entire mixture is always a relatively low number.

One significant advantage of the use of the alloys set forth in Table B is the fact that these alloys form hard and lubricious phosphide crystals at the surface of the substrate with little or no metallurgical effect on the substrate itself remaining after a reaction zone (diffusion zone) has formed. Applicant has measured the microhardness of such phosphide crystals on a substrate surface to be in the range of 1500 DPH (Diamond Pyramid Hardness), approximately equal to the Rockwell C75 hardness. Also, as compared to previously known wear resistant coatings exhibiting high lubricity, the inventive coatings include hard phosphides surrounded by softer, more ductile material to provide support and offer greater compliance.

Experimental results reveal that as compared to previously known alloy systems employed for coating and brazing, the alloys set forth in Table B provide enhanced biocompatibility, bioactivity, relatively low toxicity and enhanced wear and lubricity characteristics. Additionally, Applicant has found that the presence of Phosphorous in the alloys improves the wetting ability and enables them to wet difficult materials such as carbides and other ceramics and to perform better in brazing atmospheres which would otherwise be deemed "marginal". The Cobalt base alloys described in Table A have also been found to have enhanced corrosion resistance in certain applications.

Concerning the alloys 1, 4–6 and 13–19, as well as the compound "$Co_2P$", optimum coating conditions comprise heating to 1975° F. for 15 minutes. The alloys 3 and 7–12 in Table B require a higher melting point. With regard to alloys 3 and 7–12, it is necessary to increase the temperature to obtain full melting and adequate metallurgical mixing. On the other hand, if alloys 3 and 7–12 are exposed to 1975° F., file-like surfaces are produced since one constituent ingredient is not fully melted but is metallurgically joined to the surface. Alloys 13 and 14 are preferably used in creating a file surface while alloys 16–19 are preferably employed in making a bioactive surface, for example, for enhancement of bony ingrowth on a prosthesis. Alloys 1–3 and 12 are also useful for this purpose. Alloy 15 may be utilized in either application. When alloys 13, 14, 15, 18 and 19 are heated to 1975° F., the result described above wherein one constituent is not fully melted but is metallurgically joined to the surface occurs. This is a desired result.

In alloys 16 and 17, the specific mixture ratios are selected to produce low melting "eutectics" between the "CoP" and the Palladium or Platinum powder, as the case may be, with low melting phosphides being formed. Reaction with the substrate also lowers the required melting temperature. For example, where the substrate comprises a metal known as Ti-6Al-4V, alloys 1, 3, 12 and 16–19 as well as the "$Co_2P$" compound form low melting "eutectics" which enable coating or brazing temperatures in the range of 1900° F. to be employed. These results are possible without the presence of Nickel and this is a preferred result since it may be objectionable to employ Nickel in some biomedical applications due to the chance that an allergic reaction might result. If too high a temperature is employed, an excess reaction will occur and the properties of the coating/brazing joint may be reduced.

In a further aspect, the amount of time that the alloy is held at melting temperature is an important parameter since complete melting of the mixture must occur in some coating and brazing applications. In other applications where only partial melting is desired such as, for example, file surfaces, as explained above, the melting time must be minimized to enhance the above-described result wherein one constituent is not fully melted but is metallurgically joined to the surface.

If the time of melting is too long, excess interalloying and diffusion between the coating/braze alloy and the substrate may occur. In this way, loss of coating/braze alloy elements to the substrate may reduce the properties as well as the aesthetic appearance of the surface of the coating/braze alloy. The rate of heating of the alloy and substrate must be controlled to be sufficiently gradual enough so that preapplied powders do not dislodge from the substrate surface before melting temperature is reached. This consideration must also be balanced by the fact that processing economics dictate rates which are as fast as possible while maintaining effective coating/brazing.

The rate of cooling of the coated substrate influences crystal size. If the cooling rate after melting and bonding is too fast, crystal size will be small because crystal growth time is short and crystal nucleation dominates. Slow rates of cooling result in production of large crystals because adequate time is available for crystal growth.

The alloys and the "$Co_2P$" compound depicted in Table B are especially effective in coating substrates made up of certain materials. These substrates comprise the following families of alloys:

1. Low alloy and stainless steels where the base element is Fe and principal alloying elements are Cr, Ni, Mo, C, V, W, Si, Mn, N, Cu, S, P. Melting ranges are 2550°–2750° F. and are thus compatible.

2. Cobalt base alloys with alloying additions Cr, Mo, C, Ni, W, V, Fe, Mn, Si, Zr, Ta, Y, Cu, Ti, Al , B. Melting ranges are 2300°–2550° F. and are thus compatible.

3. Nickel base alloys with alloying additions Cr, Mo, Co, Fe, C, W, V, Al , Ti, Cu, Nb, Ta, Zr, Si, B, Mn, $Y_2O_3$. Melting ranges are 2300°–2500° F. and are thus compatible.

4. Titanium base alloys with additions Al , V, Nb, Sn, Cr, Mo, O, N, Mn, Ni, Cu, Si, C, Fe, Zr, Ta. Melting ranges are 2800°–3000° F. and are compatible.

Through experimentation, Applicant has developed various appropriate applications for the alloys depicted in Table B. Applicant has found the following:

(1) Alloys 1 and 3–11 as well as the compound "$Co_2P$" are suitable for coating or brazing on wear surfaces such as surgical blades, cutting and drilling guides, drills, oil well equipment and bearings. Each of these environments requires hard lubricious surfaces which are formed in accordance with the teachings of the present invention.

(2) Alloys 7–15 have been found useful to produce abrasive surfaces which are needed for files, burrs and cutting tools.

(3) Alloys 1, 3, 12 and 15–19 as well as the compound "Co$_2$P" have been found useful to coat prostheses to promote bone ingrowth and adherance through formation of biocompatible phosphides.

(4) Alloys 1, 3–12, 15–19 and the compound "Co$_2$P" have been found useful in brazing components together to form assemblies used as medical devices and general substrate materials.

As explained above, the alloys identified in Table B by the numbers 7–15 are especially suitable for use in providing abrasive surfaces for file blades. These abrasive surfaces are generated by brazing discrete powder particles to the substrate surface. The powders may be produced by atomizing or crushing from a solidified melt, as explained above. Alloy 15 is especially hard and tough due to the incorporation of Tribaloy-400 which comprises a Cobalt base material generally used for plasma spraying in fine mesh size to develop a wear resistant surface. In the application described herein, this same powder is applied but in a coarse mesh size (circa −50 mesh) and is intentionally left separated to provide a highly abrasive surface. This type of powder has less tendency to undergo particle fracture, a property which is common with harder but more brittle particles such as those formed of diamond and carbides.

In an alternative application, carbide particles such as Tungsten carbide coated with Cobalt are used. These types of coatings are identified by alloy numbers 13 and 14 in Table B and provide increased resistance to particle fracture.

The mechanized and hand operated file blades which are coated in accordance with the teachings of the present invention are normally provided for bone shaping and reduction in orthopedic surgery. In these applications, biocompatibility is quite important and, therefore, a Cobalt base brazing alloy utilizing Phosphorous for melting point depression is used to join the particles to the substrate surface. As understood from Table B, the braze alloy may be combined with other commercially available braze alloys to provide other properties such as increased hardness and fracture resistance. Other commercially available braze alloys are chosen for their respective abilities to form phosphides, silicides, borides and carbides on particle surfaces during the brazing process. If desired, the Titanium-Cobalt "eutectic" may also be employed for the brazing alloy. The preferred environment of brazing comprises a vacuum furnace.

For various file applications, especially medical applications, the file blade may be provided with numerous perforations to allow "chambers" which facilitate removal of material debris. The perforations allow material to be extruded from the file/substrate interface during filing and thereby prevents filling of the low regions of the file and improves filing efficiency. Such perforations are particularly illustrated in the FIG. 2 photomicrograph. Additionally, these perforations give the operator instantaneous feedback on how much material is being removed from the substrate during each reciprocation of the file.

If desired, perforations may be provided and abrasive particles may be brazed only around the respective peripheries of the perforations so that even more low lying surface area is provided for debris circulation and removal.

Hereinabove, the optimum coating/brazing temperature ranges have been described in detail. As should be understood, in coating or brazing the alloys described in Table B as well as the compound "Co$_2$P", the alloy or compound is provided in powder form controlled to a specific mesh size based upon the application and dusted on the substrate surfaces at appropriate locations thereon. The powder is held in place by a pre-applied binder material which dissipates during the heating step.

The substrate is held in a fixture specifically designed for the particular application and is heated in a furnace having either an inert atmosphere or a vacuum until the alloy or compound is melted and metallurgically alloyed with the surface of the substrate, for example, a blade, a file, blade guide, etc.

Various metallic phosphides are formed on the new surface of the substrate. These phosphides are combinations of Cobalt phosphide and other phosphides such as Iron phosphide and other metallic phosphides from the substrate and additional coating powder elements. These phosphides are responsible for the improved wear resistance and lubricity which the substrate gains.

Additionally, any debris which is generated under use is superior in biocompatibility as compared to Nickel base coatings.

In a further aspect, phosphides are desirable surface compounds since some have a similar crystal structure to bone and hydroxyl apatite (HA). Based upon these similarities, growth of bone on coated surfaces is encouraged and the problem of absorption is avoided. The phosphides which are created in accordance with the teachings of the present invention have been selected from metals that are known to have minimal or no reported allergic or toxilogical reaction with biological systems. These phosphides include Cobalt phosphide, Titanium phosphide, Tin phosphide, Iron phosphide, Platinum phosphide and Palladium phosphide.

Other phosphides that may form with less determined response include Chromium phosphide, Nickel phosphide and Molybdenum phosphide.

Substrates which have been examined and which have been effectively coated in accordance with the teachings of the present invention include Cobalt-Chromium-Molybdenum (Co-Cr-Mo), Titanium-6 Aluminum-4 Vanadium (Ti-6-4), and stainless steel. For example, the application of "CoP" powder to the Ti-6-4 surface followed by heating in a vacuum furnace results in Titanium and Cobalt phosphides at the substrate surface. Coating powders may also be mixed with HA, applied to the prosthesis surface and metallurgically reacted to result in a composite coating with HA particles intact and mixed with phosphides.

Applicant has found that numerous application techniques may be successfully employed in applying the alloys and compound set forth in Table B on a substrate. These techniques include powder coating utilizing atomized alloy powder and/or phosphide compounds, plating "CoP", cathodic arc deposition, chemical vapor deposition, plasma arc deposition and sputtering. In each case, bonding and phosphide formation may be enhanced by heating to high temperatures in a vacuum or inert gas furnace. Subsequent treatments may also be employed to improve coating properties. For example, Chromium may be diffused into the coated surface before or after coating to improve corrosion resistance.

The following examples should in no way be considered to be limiting of the various aspects of the present invention.

EXAMPLE 1

In this example, a surgical saw blade made of a stainless steel alloy is coated with a mixture of 75%, by weight, CoP and 25%, by weight, Nicrobraz 50. This alloy is alloy 4 in Table B. The coating was created by first applying alloy powders to the surfaces of the surgical saw blade and retaining the powders in place through the use of a binder. The blade with the powders applied thereto was heated in a vacuum furnace to 1975° F. for 15 minutes to form the coating. As shown in FIG. 1, the coating is metallurgically bonded to and interalloyed with the blade surfaces. The left-hand side of the FIG. 1 photomicrograph shows a secondary electron image on the left-hand side and a back-scattered X-ray image on the right-hand side to highlight the formation of a semi-continuous phosphide phase (the gray phase on the right-hand side). Chemical analysis of the coating shows the presence of substrate elements which illustrates interalloying during the coating process. The coating of Example 1 was tested in a wear test against a similarly coated surface and there was essentially no significant wear as compared to an uncoated control test. Table C shows this data.

TABLE C

Surgical Blade Wear Test Results in Slotted Guide Tests

| Test Type | Blade Wear | Guide Wear | Total Wear | Debris |
|---|---|---|---|---|
| Uncoated Blade and Guide | 18.1 mg | 6.0 mg | 23.6 mg | 16.9 mg |
| Coated Blade and Guide | 5.4 mg | 3.0 mg | 8.4 mg | 5.0 mg |

EXAMPLE 2

Figure 2:
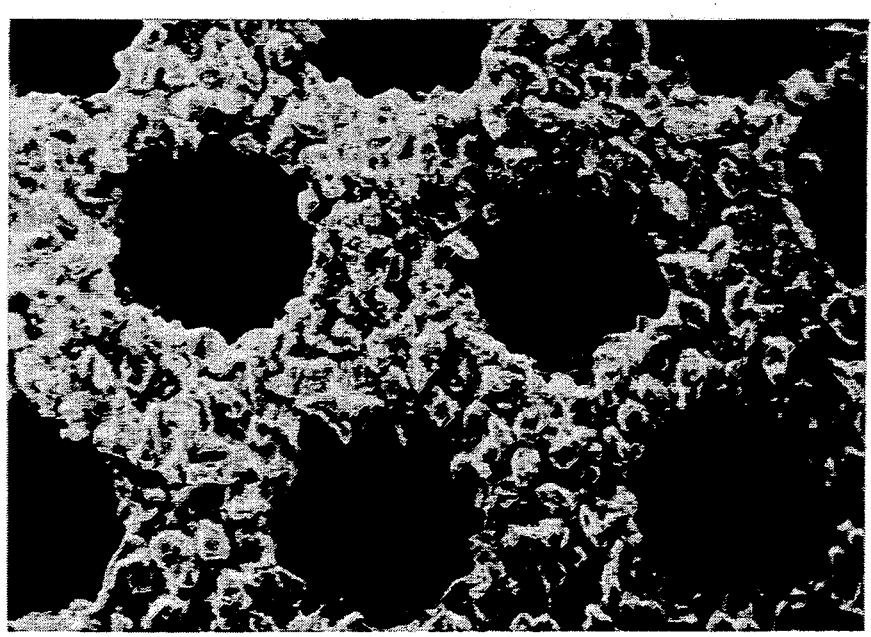
FIG. 2 shows particles of Tungsten Carbide with Cobalt binder joined to the surface of a perforated file blade with "CoP" alloy, at 20× magnification.
Figure 3:
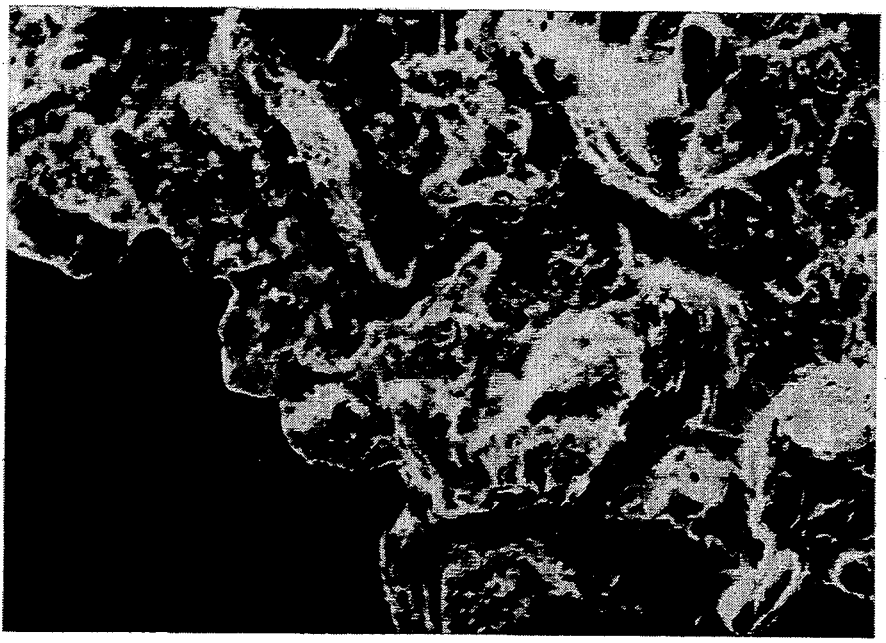
FIG. 3 shows particles of Tungsten Carbide with Cobalt binder joined to the surface of a perforated file blade with "CoP" alloy, at 80× magnification.

In this example, "CoP" alloy was employed in equal amounts, by weight, with Tungsten Carbide and applied with Cobalt binder to the surface of a file blade. This alloy is identified as alloy 14 in Table B. After application, an overcoating of "CoP" was provided. The file blade was heated to a temperature of 1975° F. for 15 minutes in a vacuum furnace. The procedure was then repeated to improve bonding. FIGS. 2 and 3 comprise photomicrographs depicting the results of carrying out the process described in Example 2. The photomicrographs illustrate good wetting, coating and metallurgical bonding of the abrasive particles. The "CoP" alloy is more biocompatible than others which have been used in the past for this purpose.

EXAMPLE 3

Figure 4:
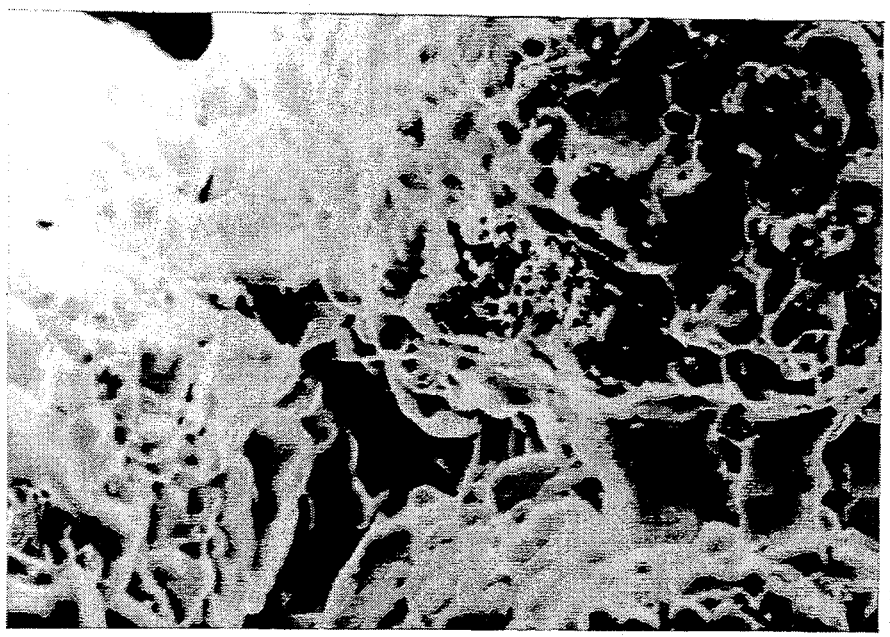
FIG. 4 shows "CoP" alloy used to join T-400 beads to a surface, at 200× magnification.
Figure 5:
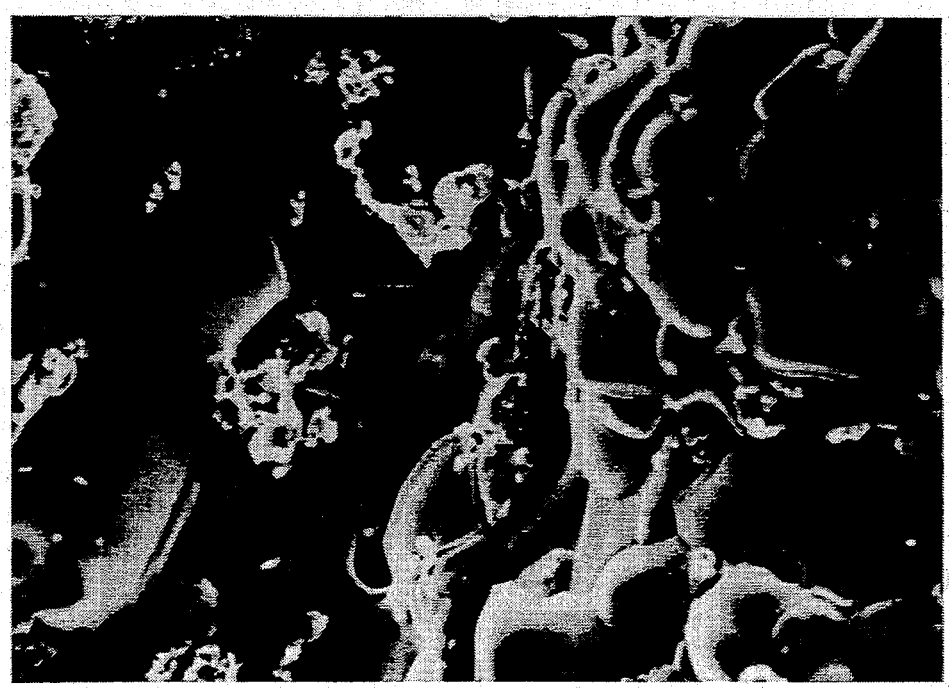
FIG. 5 shows "CoP" alloy used to join T-400 beads to a surface, at 1000× magnification.

In this example, "CoP" alloy is employed to join spherical beads of Tribaloy-400 to a substrate to form a bioactive surface. This alloy is identified by number 15 in Table B. As described in Example 2, after application on the substrate, an overcoating with "CoP" is applied. The substrate and alloy are heated in a vacuum furnace to 1975° F. to form the coating. FIGS. 4 and 5 are photomicrographs depicting the results from carrying out of this process. As should be understood from these photomicrographs, the irregular contour and increased surface area encourage bone ingrowth. Attachment is improved with this technique as compared to others since fillets are formed at the bead/substrate junctions. Additionally, phosphides are formed on the bead surfaces that enhance bone attachment and growth due to similarity in crystal structure and presence of Phosphorous. Attachment in this manner is expected to be more permanent and absorption is considered to be more limited as compared to other coatings which were previously known such as, for example, hydroxylapatite since, in this case, metal phosphides are present.

Table D depicts tensile shear data for joints made for some of the Cobalt base alloys incorporated in the present invention. As shown, good mechanical properties are demonstrated.

TABLE D

Tensile Shear Test Results of Braze Joints in Type 420 Stainless Steel

| Alloy Mixture Used to Make Test Joint, % by weight | Average Shear Stress at Failure |
|---|---|
| 100% of Alloy comprised of 89% Co - 11% P | 13,425 psi* |
| 75% of Alloy comprised of 89% Co - 11% P plus 25% of Nicrobraz 50 | 20,335 psi |
| 75% of Alloy comprised of 89% Co - 11% P plus 25% of Nicrobraz 125 | 27,310 psi |

*psi = pounds/inch$^2$

Accordingly, an invention has been described in terms of various Cobalt base alloys and the processes of coating/brazing them. As described above, these inventions demonstrate great novelty and utility.

Of course, various changes, modifications and alterations in the teachings of the present invention may be contemplated by those skilled in the art without departing from the intended spirit and scope thereof. For example, the inventive coatings are equally effective as braze materials. Additionally, the inventive compositions perform equally well when used with ceramic materials. As such, it is intended that the present invention only be limited by the terms of the appended claims.

We claim:

1. A Cobalt-Phosphorous-base wear resistant substance for coating a metallic substrate comprising a first alloy mixed with a second alloy, the first alloy being comprised of about 89%, by weight, Cobalt and about 11%, by weight, Phosphorous, the second alloy comprising a Nickel base alloy having at least 60%, by weight, Nickel, said substance containing about 75–90%, by weight, of said first alloy and about 10–25%, by weight, of said second alloy.

2. The substance of claim 1, wherein said second alloy includes, by weight, about 73.3% Ni, 14% Cr, 4.5% Si, 3% B, 4.5% Fe and 0.7% C.

3. The substance of claim 1, wherein said second alloy includes, by weight, about 94.54% Ni, 3.5% Si, 1.9% B and 0.06% C.

4. The substance of claim 1, wherein said second alloy includes, by weight, about 65% Ni, 25% Cr and 10% P.

5. The substance of claim 1, wherein said second alloy includes, by weight, about 71% Ni, 19% Cr and 10% Si.

6. The substance of claim 1, wherein said second alloy includes, by weight, about 76.2% Ni, 13% Cr, 4% Si, 2.8% B and 4% Fe.

7. The substance of claim 1, wherein said second alloy is made up of two suballoys intermixed, including a first suballoy including, by weight, about 76% Ni, 14% Cr and 10% P, and a second suballoy including, by weight, about 73.3% Ni, 14% Cr, 4.5% Si, 3% B, 4.5% Fe and 0.7% C, said second alloy being created by intermixing about 60% of said first suballoy with about 40% of said second alloy.

8. The substance of claim 1, containing about 75% of said first alloy and about 25% of said second alloy.

9. The substance of claim 8, wherein said second alloy includes, by weight, about 76% Ni, 14% Cr and 10% P.

* * * * *